(12) United States Patent
Faulkner et al.

(10) Patent No.: US 6,713,509 B1
(45) Date of Patent: Mar. 30, 2004

(54) CONTROLLED RELEASE FORMULATION FOR TREATING COPD

(75) Inventors: Patrick G. Faulkner, Collegeville, PA (US); Jaime J. Lucca, Phoenixville, PA (US); Thomas J. Wrzosek, Downingtown, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/913,997

(22) PCT Filed: Feb. 22, 2000

(86) PCT No.: PCT/US00/04713
§ 371 (c)(1),
(2), (4) Date: Aug. 22, 2001

(87) PCT Pub. No.: WO00/50011
PCT Pub. Date: Aug. 31, 2000

Related U.S. Application Data

(60) Provisional application No. 60/121,291, filed on Feb. 23, 1999.

(51) Int. Cl.$^7$ .............................................. A61K 31/275
(52) U.S. Cl. ....................... 514/520; 514/522; 514/523; 514/524; 514/525; 514/826; 424/457; 424/458; 424/462; 424/468; 424/469; 424/470; 424/486; 424/487; 424/490; 424/497
(58) Field of Search ................................ 514/520, 522, 514/523, 524, 525, 826; 424/457, 458, 462, 468, 469, 470, 486, 487, 490, 497

(56) References Cited

U.S. PATENT DOCUMENTS

| | | | |
|---|---|---|---|
| 5,286,494 A | 2/1994 | Fechner et al. | 424/490 |
| 5,998,428 A | 12/1999 | Barnette et al. | 514/285 |

*Primary Examiner*—Frederick Krass
(74) *Attorney, Agent, or Firm*—James M. Kanagy; Stephen Venetianer; Charles M. Kinzig

(57) ABSTRACT

This invention relates to a controlled or sustained release formulation designed to deliver a PDE4 inhibitor for treating an inflammatory disease such as asthma or COPD and the like.

4 Claims, 3 Drawing Sheets

DESIGN-EXPERT Plot

Actual Components:
X1 = Avicel
X2 = Carbopol 971
X3 = Carbopol 974

Actual Constants:
Drug = 10.00
A-Tab = 114.80
Lactose = 129.15

DESIGN-EXPERT Plot

Actual Components:
X1 = Avicel
X2 = Lactose
X3 = A-Tab

Actual Constants:
Drug = 10.00
Carbopol 971 = 5.00
Carbopol 974 = 8.45

CONTROLLED RELEASE FORMULATION FOR TREATING COPD

This application is a 371 of PCT/US00/04713, filed Feb. 22, 2000, which claims the benefit of Provisional Application No. 60/121,291, filed Feb. 23, 1999.

AREA OF THE INVENTION

This invention relates to a controlled or sustained release formulation designed to deliver a PDE4 inhibitor which preferentially inhibits, or binds, one form of a phosphodiesterase isozyme denominated 4 (PDE 4 hereafter) while exhibiting equal or, preferably less binding or inhibition for a second form of the enzyme.

BACKGROUND OF THE INVENTION

In the area of respiratory diseases, at least two diseases stand out as increasing in frequency and being difficult to treat, asthma and chronic obstructive pulmonary disease or COPD. While these diseases have different etiologies and different pathologies, they share a common challenge: providing effective prophylatic treatment or providing a single highly effective treatment of symptoms, particularly one with minimal side effects. One recent approach is that of a new generation of drugs targeting the cyclic nulceotide phosphodiesterases.

Cyclic nucleotide phosphodiesterases (PDEs) represent a family of enzymes that hydrolyze the ubiquitous intracellular second messengers, adenosine 3',5'-monophosphate (cAMP) and guanosine 3',5'-monophosphate (cGMP) to their corresponding inactive 5'-monophosphate metabolites. At least seven distinct classes of PDE isozymes are believed to exist, each possessing unique physical and kinetic characteristics and each representing a product of a different gene family. These are distinguished using Arabic numerals 1–7.

The target enzyme for use of the formulations of this invention is the PDE 4 isozyme in all its various forms and in the full domain of its distributions in all cells. It is a low $K_m$ (cAMP $K_m$=1–5 $\mu$M) cAMP-selective enzyme that has little activity against cGMP (Km>100 $\mu$M). Members of this isozyme class have the interesting characteristics of existing in two or more non-interconvertible or slowly interconvertible forms that bind rolipram and other PDE IV inhibitors with distinct rank-order potencies. Thus the same gene product can exist in more than one catalytically active conformational state. Importantly, the relative proportions of the different binding forms may vary depending on the tissue cell type. For example, inflammatory cells may contain a relatively high proportion of the form that binds rolipram with a low affinity while brain and parietal cells may contain a relatively high proportion of the form that binds rolipram with a high affinity. Current PDE inhibitors used in treating inflammation and as bronchodilators, drugs like theophylline and pentoxyfyllin, inhibit PDE isozymes indiscriminately in all tissues. These compounds exhibit side effects, apparently because they non-selectively inhibit all PDE isozyme classes in all tissues. The targeted disease state may be effectively treated by such compounds, but unwanted secondary effects may be exhibited which, if they could be avoided or minimized, would increase the overall therapeutic effect of this approach to treating certain disease states. Although in theory isozyme-selective PDE inhibitors should represent an improvement over non-selective inhibitors, the selective inhibitors tested to date are not devoid of side effects produced as an extension of inhibiting the isozyme of interest in an inappropriate or untargeted tissue. For example, clinical studies with the selective PDE 4 inhibitor rolipram, which was being developed as an antidepressant, indicate it has psychotropic activity and produces gastrointestinal effects, e.g., pyrosis, nausea and emesis. Indications are that side effects of denbufylline, another PDE 4 inhibitor targeted for the treatment of multi-infarct dementia, may include pyrosis, nausea and emesis as well. These side effects are thought to occur as a result of inhibiting PDE 4 in specific areas of the CNS and gastrointestinal system.

But it has been found that certain compounds which potently compete for the high affinity rolipram binding form (HPDE 4) have more side effects or more intense side effects than those which more potently compete with the LPDE 4 (low affinity rolipram binding form). Data is now available which indicate that compounds can be targeted to the low affinity binding form of PDE 4 and that this form is distinct from the binding form for which rolipram is a high affinity binder. Distinct SARs have been found to exist for inhibitors acting at the high affinity rolipram binding form versus the low affinity rolipram binding form. In addition, these two forms appear to have different functional roles. Thus compounds that interacted with the low affinity rolipram binding form appear to have anti-inflammatory activity, whereas those that interact with the high affinity rolipram binding form produce side effects or exhibit more intensely those side effects.

A useful consequence of these findings is that it is now possible to identify compounds which preferentially inhibit cAMP catalytic activity where the enzyme is in the form that binds rolipram with a low affinity, thereby reducing the side effects which apparently are linked to inhibiting the form which binds rolipram with a high affinity. This provides a superior therapeutic index vis-a-vis anti-inflammatory and\or bronchodilator activities versus side effects.

While to date no one has been able to identify a compound which is completely without unwanted CNS side effects at all possible dosage levels, at least one compound has been identified that meets the criteria described above, namely cis-4-cyano-4-[3-(cyclopentyloxy)-4-methoxyphenyl]cyclohexane-1-carboxylic acid. And while this compound has a therapeutic ratio of greater than 0.1 and can be administered orally and achieve an effective therapeutic effect in COPD at certain doses, it has been found that as blood levels increase with increased levels of dosing, undesirable side effects such as those attributed to CNS activity begin to be manifested. Increasing the initial dose has been studied to determine whether or not superior treatment can be provided by increasing blood levels at a higher concentration for a longer period of time since respiratory diseases are often chronic, not episodic. This is particularly true with COPD. It has been found that the dose level and length of effective treatment, while avoiding side effects, can be achieved by using a controlled or sustained release formulation. The controlled release formulations of this invention allow for administering in a single dosage form several times the quantity that can otherwise be administered of a PDE4 inhibitor and achieve both initial therapeutically effective blood levels and maintain these blood level for an extended period of time. PDE4 inhibitors, particularly PDE4-specific inhibitors are useful in treating other diseases especially in the areas of inflammation, (e.g., asthma, chronic obstructive pulmonary disease, inflammatory bowel disease, rheumatoid arthritis), affects related to tumor necrosis factor and to cognition impairment (e.g., multi-infarct dementia, cognitive dysfunction, or stroke). This invention is useful in treating these diseases as well. These formulations and the method described herein can be used for prophylactic treatment as well. Additional other therapeutic or prophylactic agents can be combined with a PDE4 inhibitor in these formulations as well.

SUMMARY OF THE INVENTION

In a first aspect this invention relates to a pharmaceutically formulation for treating effectively inflammation in a mammal with a PDE4 inhibitor while avoiding adverse events, the process comprising mixing a pharmaceutically acceptable excipient capable of forming a controlled-release formulation with a therapeutically effective amount of a PDE4 inhibitor, which amount if administered as an immediate release preparation would clause adverse events.

In a further aspect this invention relates to a method for administering a PDE4 inhibitor in a prophylactically effective, non-emesis-causing amount for up to about 24 hours for use in the prophylaxis of a disease susceptible of to being warded off by the administration of a PDE4 ihnibitor, which method comprises confecting said compound with at least one pharmaceutically acceptable excipient capable of forming a controlled release formulation containing said compound.

In another aspect this invention relates to an improved method for preventing the onset of or treating a human suffering from a diseases which can be treated by inhibiting the PDE 4 enzyme wherein the improvement comprises confecting and/or administering a controlled release formulation comprising said compound with at least one pharmaceutically acceptable excipient capable of forming a controlled release formulation with said compound wherein said formulation has a release profile that provides a therapeutically effective, non-emisis-causing concentration of said drug in said subject for up to about 24 hours.

In yet a further aspect, this invention relates to the manufacture of a pharmaceutically acceptable dosage form which is a controlled release formulation comprising mixing a PDE 4 inhibitor with at least one excipient capable of forming a controlled release composition with said compound wherein said dosage form has a release profile that provides a therapeutically effective, non-emisis causing concentration of said drug in said subject for up to about 24 hours.

In yet another aspect, this invention relates to a method for treating inflammation or for dilating bronchi, particularly in regards to treating asthma or COPD, by administering a controlled release formulation containing a PDE 4 inhibitor wherein said formulation has a release profile that provides a therapeutically effective, non-emisis-causing concentration of said drug in said subject for up to about 24 hours.

This invention also relates to a stable controlled release formulation comprising a Carbopol polymer, drug, dibasic calcium phosphate, optionally other excipients and between about 0.5–2.0% weight/weight of water.

DETAILED DESCRIPTION OF THE INVENTION

Figure 1:
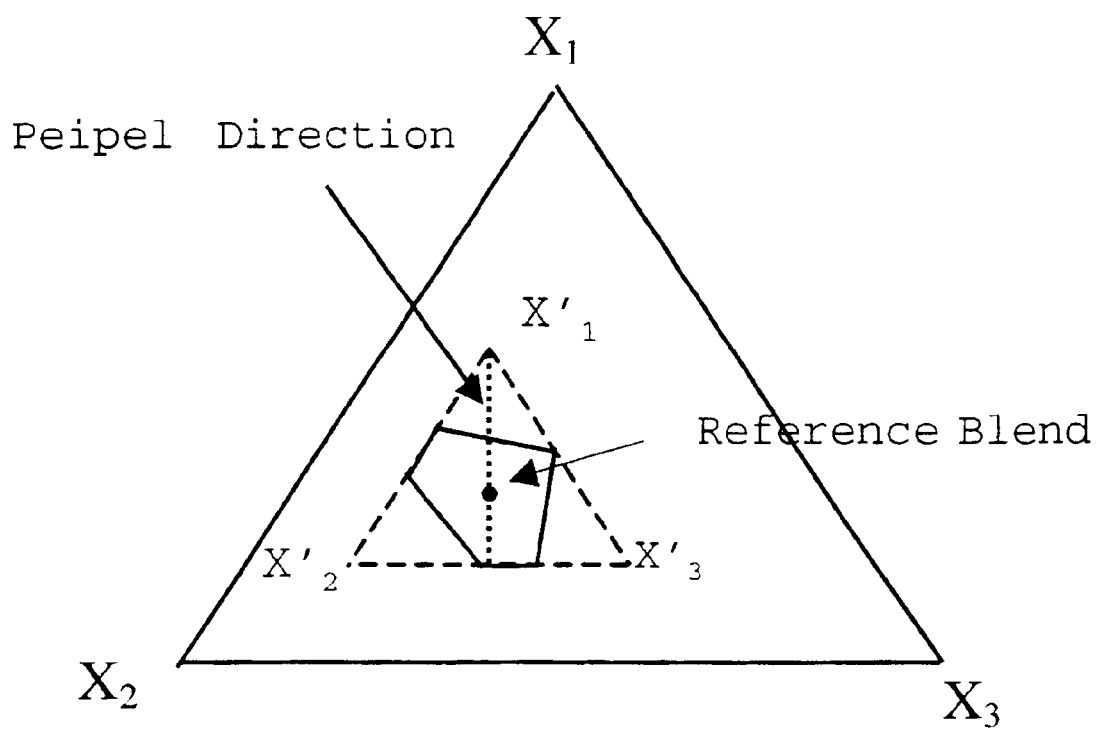
FIG. 1 is a response trace plot showing the effects of changing components.

This invention covers controlled release formulations which contain a PDE 4 inhibitor, particularly an inhibitor that is specific for PDE 4. A preferred group of inhibitors are those that have an $IC_{50}$ ratio (high/low binding) of about 0.1 or greater as further described in co-pending U.S. application Ser. No. 08/456,274, now U.S. Pat. No. 6,143,782 and its published counter-part PCT application serial number published Jan. 05, 1995 as WO95/00139; this application is incorporated herein in full by reference as if fully set forth herein. A preferred standard for PDE 4-specific inhibitors which can be used in this invention is one where the compound has an $IC_{50}$ ratio of about 0.1 or greater; said ratio being the ratio of the $IC_{50}$ value for competing with the binding of 1 nM of $[^3H]R$-rolipram to a form of PDE 4 which binds rolipram with a high affinity over the $IC_{50}$ value for inhibiting the PDE 4 catalytic activity of a form which binds rolipram with a low affinity using 1 $uM[^3H]$-cAMP as the substrate.

Other PDE 4 inhibitors that may be included in these formulations include those set out in U.S. Pat. No. 5,552,438 issued Sep. 03, 1996. This patent and the compounds it discloses are incorporated herein in full by reference. The compound of particular interest, which is disclosed in U.S. Pat. No. 5,552,438, is cis-4-cyano-4-[3-(cyclopentyloxy)-4-methoxyphenyl]cyclohexane-1-carboxylic acid and its salts, esters, pro-drugs or physical forms. Other PDE 4 inhibitors which may be of interest include: AWD-12-281 from Astra (Hofgen, N. et al. 15th EFMC Int Symp Med Chem (September 6–10, Edinburgh) 1998, Abst P.98); a 9-benzyladenine derivative nominated NCS-613 (INSERM); D-4418 from Chiroscience and Schering-Plough; a benzodiazepine PDE4 inhibitor identified as CI-1018 (PD-168787; Parke-Davis/Warner-Lambert); a benzodioxole derivative Kyowa Hakko disclosed in WO 9916766; V-11294A from Napp (Landells, L. J. et al. Eur Resp J [Annu Cong Eur Resp Soc (September 19–23, Geneva) 1998] 1998, 12(Suppl. 28): Abst P2393); roflumilast (CAS reference No 162401-32-3) and a pthalazinone (WO 9947505) from Byk-Gulden; and a compound identified as T-440 (Tanabe Seiyaku; Fujii, K. et al. *J Pharmacol Exp Ther*,1998, 284(1): 162). Preferred compounds of this invention are those which have an $IC_{50}$ ratio of greater than 0.5, and particularly those compounds having a ratio of greater than 1.0. The most preferred compounds are roflumilast and cis-4-cyano-4-[3-(cyclopentyloxy)-4-methoxyphenyl]cyclohexane-1-carboxylic acid.

Other drugs useful in treating PDE4-related diseases can be incorporated into these formulations as well. Examples of other therapeutics by category are drugs which treat: inflammatory respiratory diseases such as bronchodilators, leukotriene receptor antagonists and leukotriene biosynthesis inhibitors; non-respiratory inflammatory diseases such as irritable bowel disease (IBD); immunomodulating drugs, cognition enhancers; drugs for treating rheumatoid arthritis, rheumatoid spondylitis, osteoarthritis, gouty arthritis and other arthritic conditions; sepsis; septic shock; endotoxic shock; gram negative sepsis; toxic shock syndrome; adult respiratory distress syndrome; cerebral malaria; silicosis; pulmonary sarcoidosis; drugs for treating bone resorption diseases; reperfusion injury; graft vs. host reaction; allograft rejections; fever and myalgias due to infection, such as influenza, cachexia secondary to infection or malignancy, cachexia secondary to human acquired immune deficiency syndrome (AIDS), AIDS, ARC (AIDS related complex); keloid formation; scar tissue formation; Crohn's disease; ulcerative colitis; pyresis; autoimmune diseases such as multiple sclerosis, autoimmune diabetes and systemic lupus erythematosis; drugs for treating viral infections such as cytomegalovirus (CMV), influenza virus, adenovirus, and the herpes virus, and drugs for treating yeast and fungal infections.

Exemplary types of compounds for treating respiratory diseases are leukotriene antagonists; mucolytics; antitussives and expectorants; antibiotics; oral or inhaled beta-agonists; phosphodiesterase inhibitors other that PDE4-specific inhibitors; nasal decongestants; elastase inhibitors; protein therapeutics such as IL4, IL5, IL8, and IL13 monoclonal antibodies, anti-IgE; or oral or inhaled corticosteriods. Particularly preferred combination therapies are the use of a therapeutic amount of a corticosteriod, a beta agonist, an anticholinergic, an inhaled cromone, a leukotriene antagonist, or an antibiotic to treat secondary infections.

These preparations are termed "controlled release" formulations. This phrase is intended to cover any formulation which can be characterized as having a release profile that releases a portion of its drug load, either at several time-points or continuously over time. This type of formula is sometimes also described as a sustained release formulation or a non-immediate-release delivery system. By way of further illustration and explanation, these delivery systems can be characterized as: i) delayed release, ii) controlled or prolonged release, iii) site-specific release, or iv) receptor release. A more detailed explanation of these different systems is available in the likes of *Remington's Pharmaceutical Sciences*, 18th Edition, Mack Publishing Co. Easton, Pa., U.S.A. 18042 or later additions or *Drugs and Pharmaceutical Sciences*, v 29: "Controlled Drug Delivery : Fundamentals and Applications, Second Edition, Edited by Joseph R. Robinson and Vincent H. Lee, Published by Marcel Dekker Inc.

The preferred forms of this invention are the delayed release formulations or the controlled or prolonged release preparations which are administered orally. A suppository could be effective as well. These several systems may be dissolution-dependent, as illustrated by encapsulated dissolution products or matrix dissolution products. Or they may be formulated using osmotic systems or ion exchange resins. The most preferred approach is to provide an oral controlled release product based on matrix dissolution technology.

Controlled release preparations used in this invention can be prepared by selecting excipients from any number of materials which provide the requisite controlled release profile needed to avoid side effects while providing a useful therapeutic concentration of the drug. Without intending to be limited, a preferred approach is to use a matrix dissolution technology based on acrylic acid polymers. Carbomer is the non-proprietary name for these materials. They are high molecular weight polymers prepared by cross-linking acrylic acids with the likes of allylsucrose or allyl ethers of pentaerythritol. Such polymers also go by the names acritamer or carbopol. The chemical name and CAS registry number for the class is carboxypolymethylene [54182-57-9]. Exemplary carbomers are carbomer 910 [91315-32-1], carbomer 934 [9007-16-3], carbomer 934P [9003-01-4] and carbomer 940 [76050-42-5]. These polymers contain between 56–68% of carboxylic acid groups, calculated on a dry basis. A blend of two or more carbomers of differing molecular weight can be used to modify and manipulate the release rate. Examples are given below. In addition, the preferred formula may contain a binding agent, fillers, lubricants, and the like.

The goal is to prepare a formulation which release the drug in a manner that provides therapeutically effective concentration within a range which treats COPD, or another PDE 4-modulated disease, over a number of hours, but which is not so high that it initiates a secondary reaction such as psychotropic activity and produces gastrointestinal effects, e.g., pyrosis, nausea or emesis. Thus the active ingredient will be present in the preparation an amount sufficient to provide a concentration in the blood stream which effects a therapeutic response over a period of up to about 24 hours, measure from the time of administration of when an oral preparation is consumed. A preferred time-frame for release of drug is where the release is effected in about 12 hours. The amount of drug must necessarily depend on the potency of the drug that is being administered, its bio-availability, metabolic disposition, clearance rate and the like. A highly potent drug which is well absorbed, and not rapidly metabolized or cleared from the system will necessarily dictate a concentration on the lower end of the spectrum of a continuum of possible drug load that can be accommodated by a given set of excipients. A compound which requires a higher concentration to effect a therapeutic response, or which is not absorbed well will need to be present in a higher concentration. Precise parameters can not be set forth for all compounds; some testing and modification of excipient and drug will be useful in optimizing the amount and release rate of a given formulation for the active compounds intended to be covered by this invention.

For the purposes of this invention, it is preferred to manufacture a product which contains between about 1 mg to 200 mg, more preferably 5 to 100 mg, most preferably between 5, or 10 to 60 mg of the active ingredient. Additional preferred dosage amounts are about within these ranges are 10, 15, 20, 30, 40, 50, 60, 70, 80 or 90 mg per preparation.

The preferred excipients for affecting release rate are carbomers, particularly a combination of two or more different carbomers. Especifically preferred are those carbomers known as Carbopols and are manufactured by BF Goodrich. Preferred carbomers are: Carbomer 934P (Carbopol 974P) and Carbomer 941P (Carbopol 971P).

A preferred formulation will have between about 1–25% by weight of a PDE 4 inhibitor, preferably an amount between 3–20% and optionally an amount between about 5 and 15%. Other specific amounts are set out in the Examples below. In regards to the carbomers, one or more may be used to realize the controlled release effect. It is preferred to use two carbomers in a given formulation. When a preferred formulation containing the acid set out above is prepared, one or both of two carbomers is used in a range between 0–9% each. These percentages are weight/weight percentages. Further specific preferred percentages of carbomers are given in the Examples set out below.

The following examples are provided to illustrate how to make and use the invention. They are not in any way intended to limit the scope of the invention in any manner or to any degree. Please refer to the claims for what is reserved to the inventors hereunder.

EXAMPLE 1

Experimental Design

The six direct compression components which were investigated in the study included the drug and five excipients. These components 1% w/w of magnesium stearate made up the formula. The five excipients were carbopol 971P, carbopol 974P, (manufactured BF Goodrich), lactose anhydrous direct tableting, dibasic calcium phosphate anhydrous and microcrystalline cellulose. Upper restraints were put on all the excipient components.

The component levels can be expressed in three different ways. First they can be expressed in terms of the actual components. In this case they would be expressed in mg. Real values are the components expressed as percents or fractions of the total components:

Real=Actual/(total of actuals)

$R_i = A_i / \Sigma A_i$

The last component values are called Pseudo components. Pseudo components are defined as:

Pseudo=(Real−$L_i$)/(1−L)

where $L_i$=lower constraint in real value and L=sum of lower constraints in real values Pseudo components are generally used when fitting models because of better mathematical stability over the original units. Components and component restraints are summarized below in Table 1.

TABLE 1

Component restraints

| COMPONENT | Actual (mg) | Pseudo |
|---|---|---|
| Drug* | 10–40 | 0–0.105 |
| Carbopol 971P | 0–21 | 0–0.073 |
| Carbopol 974P | 0–21 | 0–0.073 |
| A-Tab | 0–281 | 0–0.979 |
| Lactose | 0–281 | 0–0.979 |
| Avicel PH102 | 0–45 | 0–0.157 |

*cis-4-cyano-4-[3-(cyclopentyloxy)-4-methoxyphenyl]cyclohexane-1-carboxylic acid

EXAMPLE 2

Experimental Run Selection

A list of candidate points was generated. The list included extreme vertices, centers of edges, face centroids, axial centers, and the overall centroid. The number of runs was decided on by the type or degree of model to be fitted. A second-order design with 6 components contains 21 terms. At least as many design points as terms was needed to fit the model. Adding additional points for error estimation and model lack of fit testing brings the total to 28 runs. Starting with the candidate list of points and using a D-optimality program, the set of points that minimizes the variance of the fitted model coefficients were selected. The runs that were selected are listed in Table 2.

EXAMPLE 3

Preparation of Controlled Release Formulation

Blending

The blends were made up in accordance with Table 2, excipients and drug were placed in a blender and mixed. The magnesium stearate was then added and mixed for an additional 3 minutes. During the blending process, excipients and drug were mixed, passed through a screen and then mixed again.

Compression

Approximately 350 mg of each mix was compressed into tablets. A target tablet strength of 10 kp was used.

EXAMPLE 4

Physical Measurements—Dissolution

Three compacts of each formula were prepared for dissolution. These were run using USP Apparatus II, 50 rpm, paddles, 900 ml of pH 7.5 buffer. Samples (20 ml, volume replaced) were taken at 1, 3, 5, 8 and 12 hours and then analyzed for cis-4-cyano-4-[3-(cyclopentyloxy)-4-methoxyphenyl]cyclohexane-1-carboxylic acid using UV.

EXAMPLE 5

Analysis of Release Rates: Model Fitting—Dissolution Slope

The response % dissolved was found to have a linear relationship to time (hr.). There for the response used to access dissolution was the slope of the dissolution curve, expressed as %/hr.

The model fitted to the data was a second order Scheffe model of the form:

TABLE 2

Experimental Run Treatment Combinations in Real Components

| Std Ord | Run No. | Type | A:Drug* | B:Carbopol 971 | C:Carbopol 974 | D:A-Tab | E:Lactose | F:Avicel |
|---|---|---|---|---|---|---|---|---|
| 20 | 1 | CentEdge | 10 | 0 | 13.5 | 0 | 228.5 | 45 |
| 25 | 2 | Vertex | 10 | 0 | 21 | 266 | 0 | 0 |
| 13 | 3 | PlaneCent | 25 | 13.5 | 0 | 0 | 258.5 | 0 |
| 23 | 4 | AxialCB | 17.5 | 13.875 | 3.375 | 59 | 169.5 | 33.75 |
| 16 | 5 | Vertex | 10 | 6 | 0 | 236 | 0 | 45 |
| 2 | 6 | Vertex | 40 | 21 | 0 | 0 | 236 | 0 |
| 7 | 7 | Vertex | 40 | 0 | 21 | 191 | 0 | 45 |
| 12 | 8 | PlaneCent | 25 | 0 | 6 | 243.5 | 0 | 22.5 |
| 5 | 9 | Vertex | 40 | 0 | 21 | 0 | 191 | 45 |
| 18 | 10 | PlaneCent | 40 | 10.5 | 10.5 | 0 | 213.5 | 22.5 |
| 10 | 11 | CentEdge | 10 | 0 | 21 | 110.5 | 110.5 | 45 |
| 26 | 12 | PlaneCent | 25 | 10.5 | 10.5 | 251 | 0 | 0 |
| 6 | 13 | Vertex | 10 | 0 | 21 | 0 | 266 | 0 |
| 9 | 14 | CentEdge | 40 | 0 | 21 | 118 | 118 | 0 |
| 19 | 15 | Vertex | 10 | 0 | 6 | 281 | 0 | 0 |
| 27 | 16 | Vertex | 10 | 0 | 6 | 281 | 0 | 0 |
| 1 | 17 | Vertex | 10 | 21 | 0 | 0 | 221 | 45 |
| 17 | 18 | Vertex | 40 | 6 | 0 | 251 | 0 | 0 |
| 3 | 19 | Vertex | 10 | 21 | 0 | 221 | 0 | 45 |
| 8 | 20 | CentEdge | 40 | 21 | 0 | 95.5 | 95.5 | 45 |
| 15 | 21 | PlaneCent | 25 | 10.5 | 10.5 | 251 | 0 | 0 |
| 21 | 22 | Vertex | 40 | 0 | 6 | 0 | 251 | 0 |
| 28 | 23 | Vertex | 40 | 6 | 0 | 251 | 0 | 0 |
| 4 | 24 | Vertex | 10 | 0 | 21 | 266 | 0 | 0 |
| 24 | 25 | AxialCB | 32.5 | 3.375 | 13.875 | 154.5 | 59 | 33.75 |
| 11 | 26 | CentEdge | 10 | 6 | 0 | 0 | 258.5 | 22.5 |
| 22 | 27 | AxialCB | 17.5 | 13.875 | 3.375 | 192 | 59 | 11.25 |
| 14 | 28 | CentEdge | 10 | 21 | 0 | 133 | 133 | 0 |

$$y = \beta_1 x_1 + \beta_2 x_2 + \beta_3 x_3 \ldots + \beta_{12} x_1 x_2 + \beta_{13} x_1 x_3 + \beta_{23} x_2 x_3 \ldots$$

where $x_i$ are the component fractions $\beta_i$ coefficients represent linear blending of the components. When only linear blending is present the response for any given blend is the sum of each component contribution. $\beta_{ij}$ terms represent nonlinear blending. These second order nonlinear terms represent either synergism or antagonism between the two components.

The final model after reduction of non-significant terms is presented in Table 3. All of the linear blending terms and eight second order terms were included in the model. This model was formed after the exclusion of three run results based on their high residuals. The explanation for these outliers was that for some of the formulations the tablets broke apart suddenly, rather than remained intact as did the majority of formulations.

TABLE 3

Design-Expert output 2'd order Scheffe Model-Dissolution

ANOVA for Mixture Reduced Quadratic Model

| Source | Sum of Squares | DF | Mean Square | F Value | Prob > F |
|---|---|---|---|---|---|
| Model | 966.74 | 13 | 74.36 | 134.49 | <0.0001 |
| Residual | 6.08 | 11 | 0.55 | | |
| Lack of Fit | 4.52 | 7 | 0.65 | 1.66 | 0.3274 |
| Pure Error | 1.56 | 4 | 0.39 | | |
| Cor Total | 972.82 | 24 | | | |

| | | | | |
|---|---|---|---|---|
| Root MSE | 0.74 | R-Squared | 0.9937 | |
| Dep Mean | 9.76 | Adj R-Squared | 0.9864 | |
| C.V. | 7.62 | Pred R-Squared | 0.9584 | |

| Component | Coefficient Estimate | DF | Standard Error | t for H₀ Coeff = 0 | Prob > |t| |
|---|---|---|---|---|---|
| A-Drug | 66.94 | 1 | 13.10 | Not | Applicable |
| B-Carbopol 971 | -579.21 | 1 | 104.62 | Not | Applicable |
| C-Carbopol 974 | 219.63 | 1 | 12.52 | Not | Applicable |
| D-A-Tab | 4.43 | 1 | 0.73 | Not | Applicable |
| E-Lactose | 4.16 | 1 | 1.12 | Not | Applicable |
| F-Avicel | 66.38 | 1 | 9.83 | Not | Applicable |
| AC | -1342.97 | 1 | 178.59 | -7.52 | <0.0001 |
| AD | -62.27 | 1 | 14.55 | -4.28 | 0.0013 |
| BC | -3549.35 | 1 | 411.12 | -8.63 | <0.0001 |
| BD | 717.19 | 1 | 125.77 | 5.70 | 0.0001 |
| BE | 589.14 | 1 | 121.61 | 4.84 | 0.0005 |
| CF | -435.26 | 1 | 151.08 | -2.88 | 0.0149 |
| DE | -11.62 | 1 | 2.77 | -4.20 | 0.0015 |
| DF | -54.08 | 1 | 9.48 | -5.71 | 0.0001 |

There exists strong correlations among the coefficients of the model. This is due to the wide disparity in the constraint ranges. The resulting design space is a narrow sliver with very poor design properties. The practical result is that some terms can be interchanged with little effect on the apparent fit of the model. Model interpretation is best done graphically by representing the predicted response as a function of the components.

Summary statistics for the model are summarized in Table 3 above. The statistics indicate no lack of fit for the model. The adjusted R-square was 0.986, which means that almost all of the variation in the data is explained by the model.

EXAMPLE 6

Model Interpretation—Component Effects, Dissolution

There are two graphical representations based on the prediction model that are useful in understanding the effects of changing the component amounts. The two graphical tools are response traces plots and contour plots. Response trace plots show the effects of changing each component along an imaginary line from a reference blend to the L-pseudocomponent system lower bound vertex. This directional change in composition called "Piepels Direction" is illustrated in FIG. 1 with a dashed line.

Figure 2:
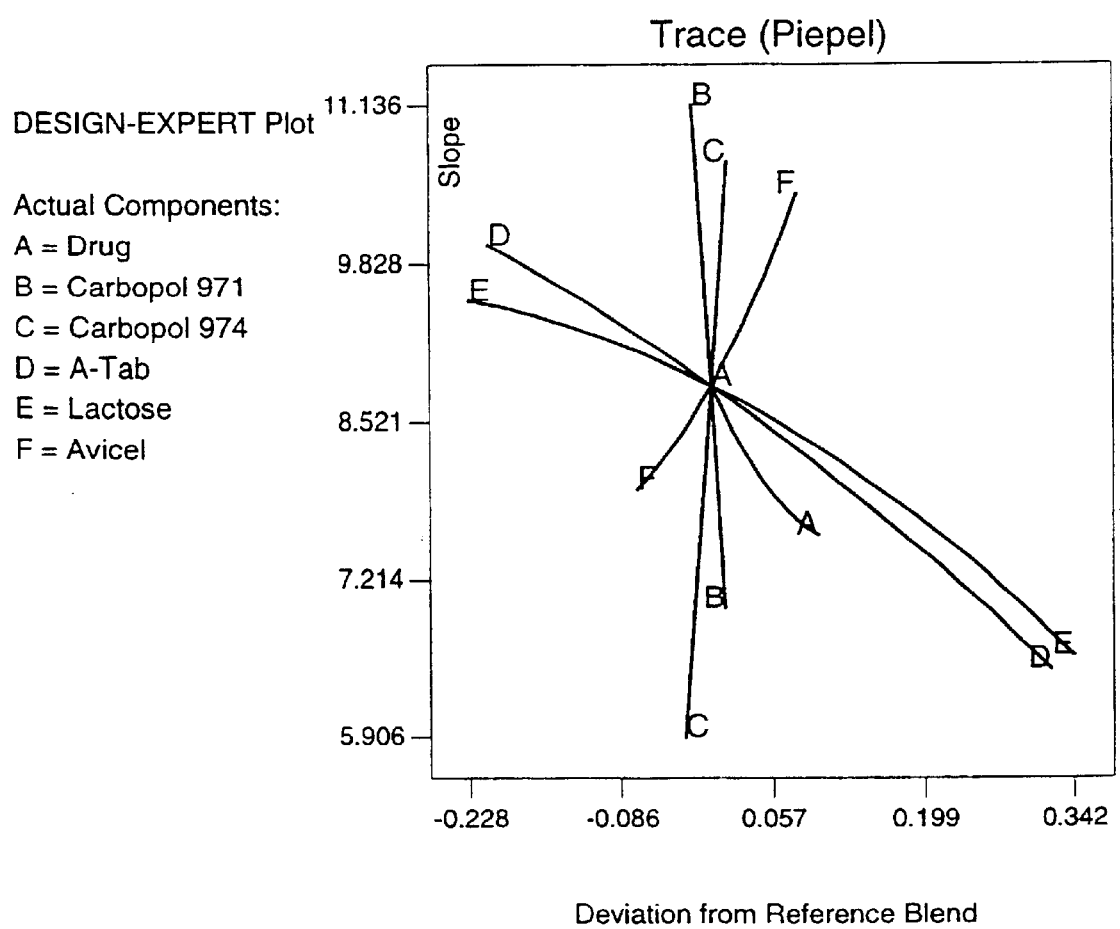
FIG. 2 shows the response traces for six components of a controlled release formulation.

FIG. 2 shows the response traces for all six components. The X-axis represents the change of that component over its range in the design space from low to high in relationship to the reference blend. From the plot it can be seen that the two carbopols have the steepest or biggest effect on the dissolution. Their effects are opposite of one another. Increasing carbopol 971 decreases dissolution rate, while increasing carbopol 974 increases it. As more drug is added the dissolution rate decreases. Increasing A-Tab or lactose has about the same effect in decreasing the dissolution rate. And lastly increasing avicel increases the dissolution rate. The reference blend used in generating the data underlying the graphics in FIG. 2 is set out in Table 4.

TABLE 4

| Reference Blend | |
|---|---|
| Carbopol 971 | 5.00 |
| Carbopol 974 | 10.00 |
| A-Tab | 140.50 |
| Lactose | 111.57 |
| Avicel | 19.93 |

Figure 3A:
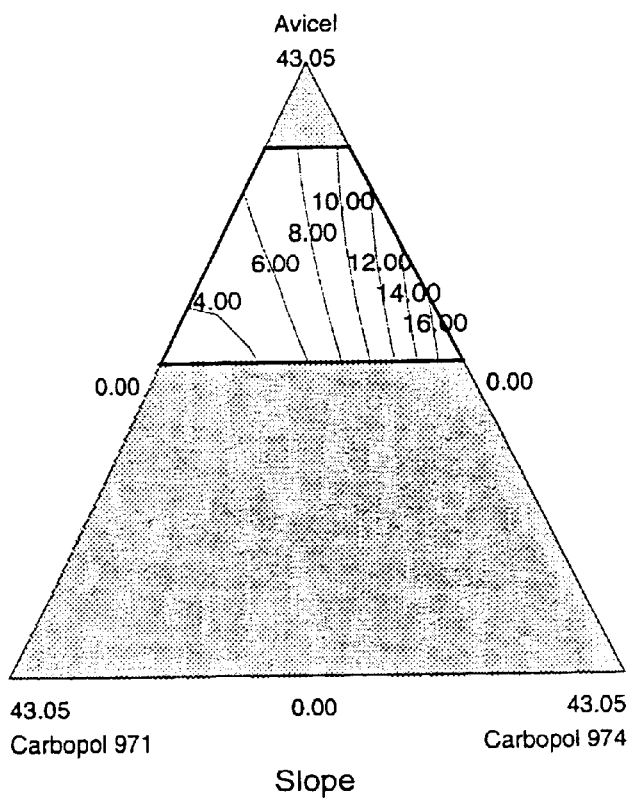
FIGS. 3A and 3B are contour plots made by using a triangulation coordination system by holding three components constant and varying three components.
Figure 3B:
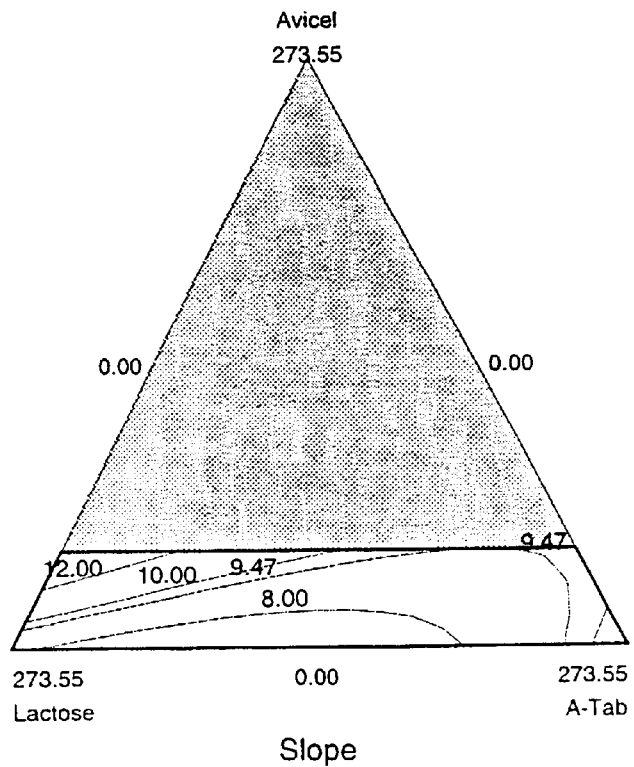

Contour plots can be made using the triangular coordinate system by holding three of the components constant and varying the remaining three. Several different contour plots are shown in FIGS. 3A and 3B. Much of the same information that is contained in the trace plots can be seen in the contour plots.

Predictions—Confirmation

Using the reduced 2'd order Scheffe model for dissolution a formula was identified to meet a target dissolution of 11%/hr (Table 5). A formula was desired that contained no lactose or avicel (microcrystalline cellulose). A predicted value of 11.45%/hr was found to be in good agreement with the actual value of 11.1%/hr.

TABLE 5

Model Predictions for Target Dissolution Formula and Results

| Component | Name | Level |
|---|---|---|
| A | Drug | 10 |
| B | Carbopol 971 | 5 |
| C | Carbopol 974 | 10 |
| D | A-Tab | 272 |
| E | Lactose | 0 |
| F | Avicel | 0 |
| | Total = | 297 |

| Parameter | Value |
|---|---|
| Prediction | 11.45 |
| SE Mean | 0.39 |
| 95% CI low | 10.59 |
| 95% CI high | 12.31 |
| SE Pred | 0.84 |
| 95% PI low | 9.6 |
| 95% PI high | 13.3 |
| Actual | 11.1 |

EXAMPLE 7

Controlled Release Formulation

Three sets of controlled release formulations were prepared using the blending and compression techniques described in Example 3. One set was formulated to give a fast release rate. The second and third formulations were designed to give a medium and slow release rate. Specific details for each set of tablets are given in Table 6.

TABLE 6

Table Ingredients

|  | Fast % w/w | Medium % w/w | Slow % w/w |
|---|---|---|---|
| Drug (SB207499) | 3.3 | 3.3 | 3.3 |
| Dibasic Calcium Phosphate (anhydrous) | 88.0 | 88.5 | 88.5 |
| Carbomer 934P | 5.4 | 3.3 | 0.0 |
| Carbomer 941P | 0.0 | 1.6 | 4.9 |
| Magnesium Stearate | 1.0 | 1.0 | 1.0 |
| Opadry White OY-S-9603 | 2.4 | 2.4 | 2.4 |
| Purified water | q.s. | q.s. | q.s. |

Opadry White was suspended in the purified water and that suspension was used to coat the tablets; water was removed during the coating process an ddid not form part of the final product.

These formulations gave in-vitro dissolution data (% released) as per Table 7.

TABLE 7

Release Profile Over Time

| Time (hrs) | Fast | Medium | Slow |
|---|---|---|---|
| 0 | 0 | 0 | 0 |
| 1 | 21 | 15.3 | 8 |
| 2 | 41 | 28 | 15 |
| 3 | 68 | 43 | 22 |
| 5 | 97 | 68 | 36 |
| 8 | 100 | 87 | 51 |
| 12 | 100 | 98 | 69 |
| 18 | — | — | 90 |
| 24 | — | — | 101 |

EXAMPLE 8

Controlled Release Formulation—Different Drug Loads

Using the experimental design techniques outlined in Example 1, multiple drug/excipient composition were identified to prepare 5 different drug concentrations which had the desired dissolution profile. Using the blending and compression techniques described in Example 3 tablets were prepared as per the ingredients and amounts set out in Table 8.

TABLE 8

Composition of Tablets

| Component | Wt of Component in Milligrams | | | | |
|---|---|---|---|---|---|
| Drug (SB207499) | 20 | 30 | 40 | 50 | 60 |
| Dibasic Ca Phosphate | 259 | 249 | 239 | 229 | 219 |
| Carbomer 934P | 9 | 9 | 9 | 9 | 9 |
| Carbomer 941P | 9 | 9 | 9 | 9 | 9 |
| Magnesium Stearate | 3 | 3 | 3 | 3 | 3 |
| Opadry White OY-S-9603 | 7.5 | 7.5 | 7.5 | 7.5 | 7.5 |
| Purified Water | q.s. | q.s. | q.s. | q.s. | q.s. |
| Total Tablet Wt. (mg) | 307.5 | 307.5 | 307.5 | 307.5 | 307.5 |

Opadry White was suspended in the purified water and that suspension was used to coat the tablets; water was removed during the coating process an ddid not form part of the final product.

A typical dissolution profile for these tablets is given in Table 9.

TABLE 9

Dissolution Profile

| Time (hrs) | % Released |
|---|---|
| 0 | 0 |
| 1 | 9 |
| 3 | 38 |
| 5 | 63 |
| 8 | 83 |
| 12 | 95 |

EXAMPLE 9

Controlled Release Formulations

Controlled release tablets were prepared containing five different drug loads. Ingredients and the amount of each ingredient per drug load are set out in Table 10. Tablets were prepared as described in Example 3.

TABLE 10

Controlled Release Formulation Preparations

| Tablet Core Components | 20 mg | 30 mg | 40 mg | 50 mg | 60 mg |
|---|---|---|---|---|---|
| cis-4-cyano-4-[3-(cyclopentyloxy)-4-methoxyphenyl]cyclohexane-1-carboxylic acid | 20.0 | 30.0 | 40.0 | 50.0 | 60.0 |
| Dibasic Calcium Phosphate, Anhydrous (A-Tab) | 259.0 | 249.0 | 239.0 | 415.0 | 498.0 |
| Carbomer 934P (Carbopol 947P) | 9.0 | 9.0 | 9.0 | 15.0 | 18.0 |
| Carbomer 941 (Carbopol 971P) | 9.0 | 9.0 | 9.0 | 15.0 | 18.0 |
| Magnesium Stearate | 3.0 | 3.0 | 3.0 | 5.0 | 6.0 |
| Tablet Core Weight - Total | 300.0 | 300.0 | 300.0 | 500.0 | 600.0 |
| Coating Component White Opadry (OY-S-9603) | 7.5 | 7.5 | 7.5 | 12.5 | 15.0 |
| AFC Tablet Weight - Total | 307.5 | 307.5 | 307.5 | 512.5 | 615.0 |

EXAMPLE 10

Stabilized Formulation

Low moisture levels in certain Carbopol-based controlled release preparations may compromise the stability of the active ingredient cis-4-cyano-4-[3-(cyclopentyloxy)-4-methoxyphenyl]cyclohexane-1-carboxylic acid. High moisture levels may compromise the release rate of such formulations. A representative controlled release formulation based on Carbopols is given in Table 1.

TABLE 11

| carboxylic acid | 30 mg |
|---|---|
| Dibasic Calcium Phosphate anhydrous (A-Tab ®) | 249 mg |
| Carbopol 971P ® | 9 mg |

TABLE 11-continued

| | |
|---|---|
| Carbopol 974P ® | 9 mg |
| Mg Stearate | 3 mg |
| Opadry ® White | 7.5 mg |
| Total | 307.5 mg |

In this examplary formulation if the moisture level falls below about 0.5%, some degradation of the acid is observed. The combination of cis-4-cyano-4-[3-(cyclopentyloxy)-4-methoxyphenyl]cyclohexane-1-carboxylic acid and dibasic calcium phosphate (anhydrous) appears to be unstable when moisture is removed from the system. Analyses of degraded tablets indicates that the cyclopentyloxy group is cleaved and results in the formation of cyclopentene and cis-4-cyano-4-[3-hydroxy-4-methoxyphenyl]cyclohexane-1-carboxylic acid. It is not known why this occurs when the moisture level is below 0.5% nor is it known how to stop this from occuring, other than to maintain the specified levels of hydration.

Conversely, if the moisture level in this formulation raises above about 2.0% the rate of release of drug substance from the tablet changes from initial.

An optimum moisture level will be in the range of about 0.8–1.3%w/w range, preferably in the range of about 0.9–1.2% w/w range. This range is applicable to the full range of concentrations of dibasic calcium phosphate present in formulations prepared within this invention.

The technique for measuring moisture level in this representative tablet was as follows:

The analysis was performed using a Omnimark MARK2 Moisture Analyzer. The Unit determines the moisture content using Infrared heat to dry the sample at a programmed temperature of 120° Celsius with a standby temperature of 80° Celsius. It calculates the percent loss on drying from the initial weight and the final weight of the sample. The results are printed out as % w/w automatically when the analysis is finished. The analysis usually takes 2 to 3 minutes for one measurement of a sample with a moisture level of less than 1.5%w/w.

A homogeneous and representative sample was used. The following sample preparation was used for each measurement:

Crush tablets to a fine powder using a mortar and pestle.

Use approximately 2 grams of sample for moisture determination.

Spread the sample evenly on the dish to obtain a thin layer that covers as much of the surface as possible.

EXAMPLE 11

Preparation of Controlled Release Beads

Nonpareil (sugar) beads are placed in a fluid bed coating machine. An aqueous suspension of cis-4-cyano-4-[3-(cyclopentyloxy)-4-methoxyphenyl]cyclohexane-1-carboxylic acid and a suitable binder (e.g. povidone or hydroxypropyl methyl cellulose) and a wetting agent if needed (e.g. tween 80) are sprayed onto the beads. A coating solution (e.g. ethylcellulose) is applied to slow the release rate of the acid. The release rate of the drug is inversely proportional to the film weight applied. These controlled release beads of the acid can then be delivered in a variet of ways to either adult or pediatric patients.

We claim:

1. A stable controlled release pharmaceutical composition comprising a controlled release excipient, dibasic calcium phosphate, a PDE4-specific inhibitor in an amount of 10 mg and 60 mg, optionally other excipients, and between about 0.5–2.0% weight/weight of water.

2. The composition according to claim 1 wherein the controlled release excipient is an acrylic acid polymer.

3. The composition of claim 1 comprising cis-4-cyano-4-[3-(cyclopentyloxy)-4-methoxyphenyl]cyclohexane-1-carboxylic acid, about 0–10% percent of carbopol 971P by weight, 0–10% percent of carbopol 974P by weight, and additional pharmaceutically acceptable excipients to make 100 percent by weight.

4. The composition of claim 3 wherein the acrylic acid polymer is present in the amount of 30 mg of 60 mg and water is present in an amount between 0.9–1.2% w/w.

* * * * *